(12) United States Patent
    Kilic

(10) Patent No.: US 12,629,044 B2
(45) Date of Patent: May 19, 2026

(54) SYSTEM AND METHOD FOR PERFORMING LASER DOPPLER FLOWMETRY

(71) Applicant: Sonion Nederland B.V., Hoofddorp (NL)

(72) Inventor: Yakup Kilic, Hoofddrop (NL)

(73) Assignee: Sonion Nederland B.V., Hoofddorp (NL)

( * ) Notice: Subject to any disclaimer, the term of this patent is extended or adjusted under 35 U.S.C. 154(b) by 0 days.

(21) Appl. No.: 19/234,899

(22) Filed: Jun. 11, 2025

(65) Prior Publication Data

US 2025/0375120 A1    Dec. 11, 2025

(30) Foreign Application Priority Data

Jun. 11, 2024    (EP) ..................................... 24181426

(51) Int. Cl.
    *A61B 5/026*    (2006.01)
    *A61B 5/00*    (2006.01)
    *A61B 5/381*    (2021.01)

(52) U.S. Cl.
    CPC ............ *A61B 5/0261* (2013.01); *A61B 5/381* (2021.01); *A61B 5/7278* (2013.01); *A61B 5/7285* (2013.01)

(58) Field of Classification Search
    CPC ..... A61B 5/0261; A61B 5/0075; A61B 5/381; A61B 5/7278; A61B 5/7285;
    (Continued)

(56) References Cited

U.S. PATENT DOCUMENTS 5,598,841 A * 2/1997 Taniji ................... A61B 5/0261
                                                            600/479
6,173,197 B1    1/2001 Bogett
                (Continued)

FOREIGN PATENT DOCUMENTS

GB          2351197 A    12/2000
JP      2014079428 A *    5/2014
                (Continued)

OTHER PUBLICATIONS

Chen, Y. Y., Lin, Y. H., Jan, I. C., Liu, R. S., Chou, N. K., & Jan, G. J. (2004). Adaptive processing bandwidth adjustment for laser Doppler flowmetry. Medical and Biological Engineering and Computing, 42(3), 277-281. (Year: 2004).*
                (Continued)

*Primary Examiner* — Keith M Raymond
*Assistant Examiner* — Johnathan Maynard
(74) *Attorney, Agent, or Firm* — Harness, Dickey & Pierce, P.L.C.

(57) ABSTRACT

The invention relates to a system and method for performing a laser Doppler flowmetry, LDF, measurement. The system comprises a coherent light source, a photodetector and one or more processors. The photodetector generates an output signal. The processor(s) determines a selected frequency range for computing an LDF signal. A spectrum of the photodetector output signal is computed for a series of time intervals, thereby obtaining a series of spectra. A measure of the amount of physiological information in the spectra is computed for a number of different frequencies. The selected frequency range is determined as the range of frequencies for which the computed measure of amount of physiological information fulfills a predetermined criterion. The processor(s) compute an LDF signal using the selected frequency range, and output the LDF signal.

8 Claims, 5 Drawing Sheets

(58) Field of Classification Search
CPC .............. A61B 5/7257; A61B 5/02108; A61B
5/02438; A61B 5/681
See application file for complete search history.

(56) References Cited

U.S. PATENT DOCUMENTS

| | | | |
|---|---|---|---|
| 7,798,968 | B2 | 9/2010 | Li |
| 10,856,751 | B2 | 12/2020 | Watanabe |
| 2019/0117171 | A1* | 4/2019 | Enari ................... A61B 5/0261 |
| 2020/0284628 | A1* | 9/2020 | Tateishi .................... G01P 5/26 |

FOREIGN PATENT DOCUMENTS

| | | |
|---|---|---|
| WO | 2016/138965 A1 | 9/2016 |
| WO | 2024/213563 A1 | 10/2024 |
| WO | 2025/068263 A1 | 4/2025 |

OTHER PUBLICATIONS

Extended European Search Report in Application No. EP 24181426.8, mailed Nov. 4, 2024.

Chen Y Y et al: "Adaptive Processing Bandwidth Adjustment For Laser Doppler Flowmetry", Medical and Biological Engineering and Computing, Springer, Heidelberg, DE, vol. 42, No. 3, May 1, 2024 (May 1, 2004), pp. 277-281, ISSN: 0140-0118, DOI: 10.1007/BF02344700.

Wojtkiewicz S et al: "Evaluation of algorithms for microperfusion assessment by fast simulations of laser Doppler power spectral density", Physics in Medicine and Biology, Institute of Physics Publishing, Bristol GB, vol. 56, No. 24, Nov. 16, 2011 (Nov. 15, 2011), pp. 7709-7723, ISSN: 0031-9155, DOI: 10.1088/0031-9155/56/24/002.

Qu Xiaofu et al: "Improvement of the detection of human pulpal blood flow using a laser Doppler flowmeter modified for low flow velocity", Archives of Oral Biology, vol. 59, No. 2, Feb. 1, 2014 (Feb. 1, 2014), pp. 199-206, GB, ISSN: 0003-9969, DOI: 10.1016/j.archoralbio.2012.11.009.

Obeid A N: "In vitro comparison of different signal processing algorithms used in laser Doppler flowmetry", Medical and Biological Engineering and Computing, Springer, Heidelberg, DE, vol. 31, No. 1, Jan. 1, 1993 (Jan. 1, 1993), pp. 43-52, ISSN: 0140-0118, DOI: 10.1007/BF02446892.

Liebert A et al: "Multichannel laser-Doppler probe for blood perfusion measurement with depth discrimination", Medical and Biological Engineering and Computing, Springer, Heidelberg, DE, vol. 36, No. 6, Nov. 1, 1998 (Nov. 1, 1998), pp. 740-747, ISSN: 0140-0118.

R. Bonner, and R. Nossal, "Model for laser Doppler measurements of blood flow in tissue", Applied Optics, vol. 20., No. 12, Jun. 15, 1981.

A. Serov, "Novel instruments for remote and direct-contact laser Doppler perfusion imaging and monitoring", PhD thesis, University of Twente, 2002.

I. Kozlov, E. Zherebtsov, K. Podmasteryev, A. Dunaev, "Laser Doppler spectrum analysis based on calculation of cumulative sums detects changes in skin capillary blood flow in type 2 diabetes melitus", Diagnostics, vol. 11(2), Feb. 2021.

Yuan-Hsiang Lin et al: "Design and Development of Laser Doppler Velocimetry Based on DSP Technique for Blood Flow Measurement", Optical Sensing, Imaging, and Manipulation for Biological and Biomedical Applications, Proceedings of SPIE vol. 4082 (2000).

* cited by examiner

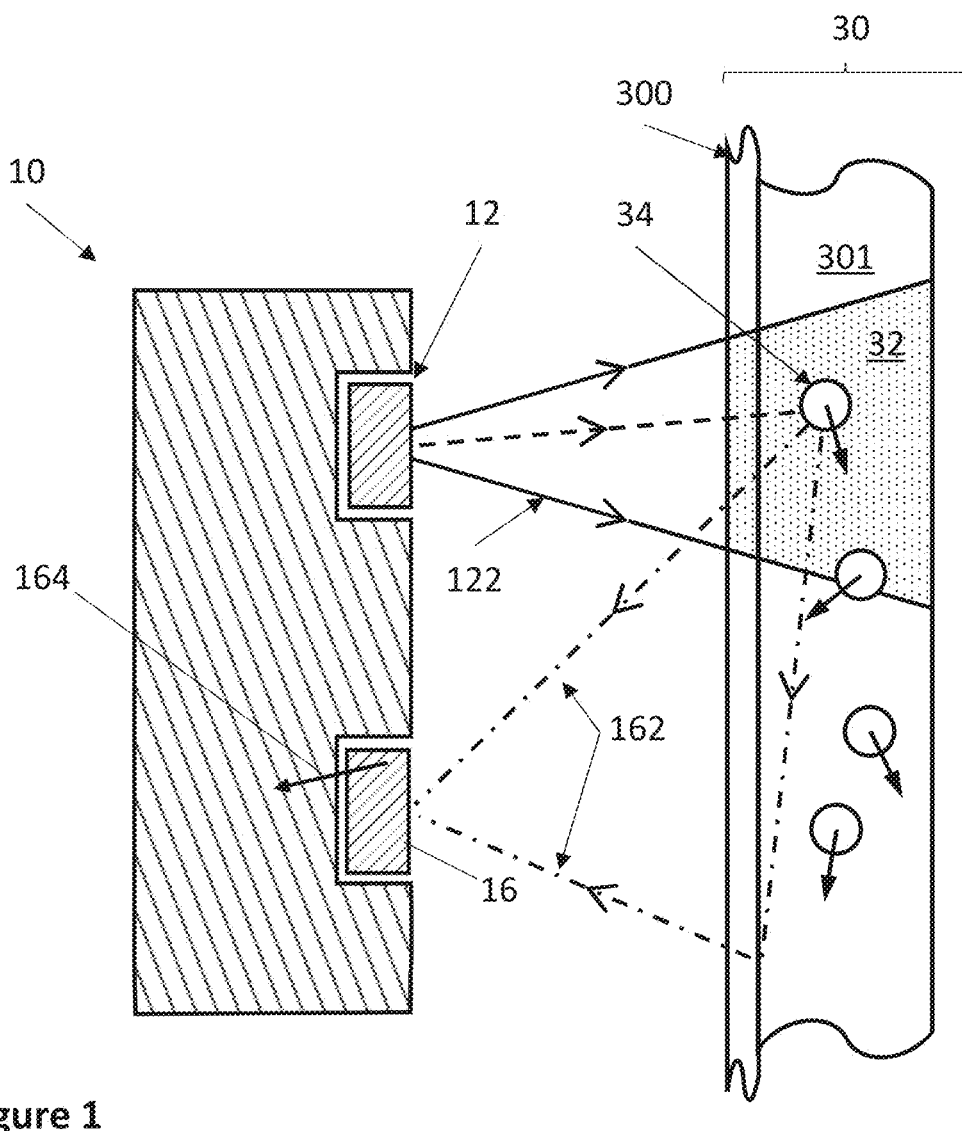
Figure 1
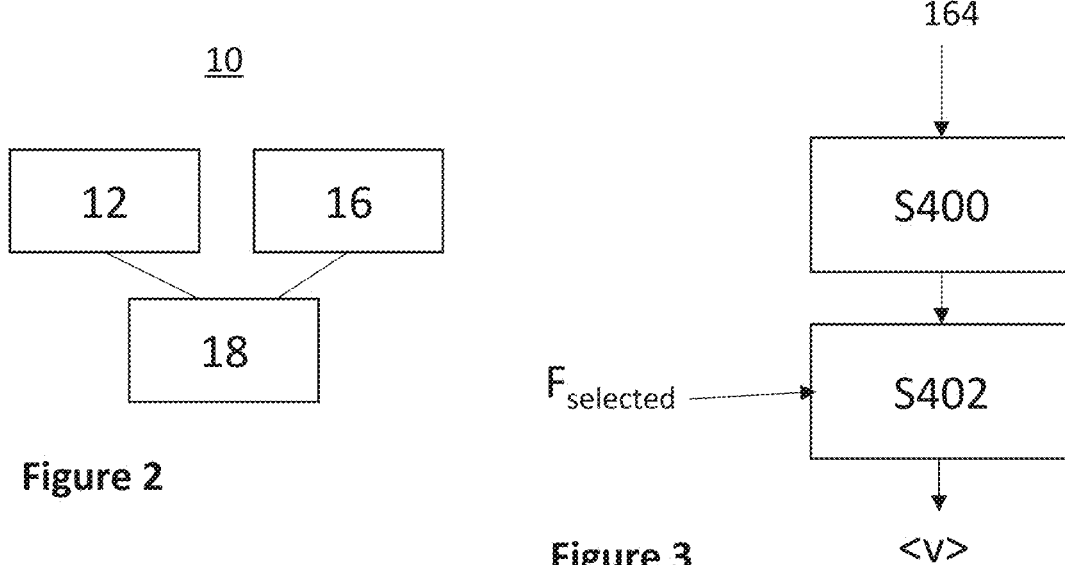
Figure 2
Figure 3

164

S400

S401

L1

S402

$<V_{Fj}>$

S408          S404          $Q_j$          $F_{selected}$

S406          S410

$<V_{Fselected}>$ $<V_{Fj}>$          S412 → S416          S420

S414 → S418

SYSTEM AND METHOD FOR PERFORMING LASER DOPPLER FLOWMETRY

CROSS-REFERENCE TO RELATED APPLICATION

This application claims priority to European Patent Application No. 24181426.8 filed on Jun. 11, 2024, the entire contents of which are incorporated herein by reference.

FIELD OF THE INVENTION

The present invention relates to a system and method for performing a laser Doppler flowmetry measurement of a blood perfused tissue.

BACKGROUND OF THE INVENTION

Laser Doppler velocimetry (LDV) is a technique to measure the velocity of a fluid. When LDV is used for measuring blood flow in a body, it is commonly referred to as laser Doppler flowmetry (LDF). The term 'velocimetry' may suggest that velocity is measured but the blood flow signal obtained by LDV is in fact a scalar and contains no direction information. The blood flow signal is therefore related to speed of the blood. For this reason, the present disclosure uses the term LDF.

DESCRIPTION OF THE INVENTION

A problem with known systems for LDF measurements is that their accuracy depends on various uncontrollable factors. The accuracy for example depends on the subject under investigation. Even LDF measurements of the same subject vary depending on e.g. the location on the subject's body. The accuracy of the measurement further changes for different average blood velocity.

An object of the invention is to overcome the drawbacks of known devices, or at least provide an alternative system. In particular, the invention aims to provide a more accurate system for LDF measurement of a blood perfused tissue.

This aim is achieved by the systems and methods according to the present disclosure.

According to the invention, the system comprises a light source configured to emit coherent light, a photodetector and one or more processors. The coherent light source, e.g. a laser, is configured to emit coherent light to the blood perfused tissue. The photodetector is configured to receive a portion of the coherent light scattered by the blood perfused tissue. The photodetector is configured to generate a photodetector output signal in response to receiving said portion. The one or more processors are configured to compute a power spectral density ($S_i(f)$) of the photodetector output signal for a series of time intervals ($t_i$), thereby obtaining a series of power spectral densities (PSDs). The one or more processors are configured to compute an LDF signal ($<v>$). Computing the LDF signal ($<v>$) comprises computing a moment ($M_i$) of each of the PSDs ($S_i(f)$). The moments ($M_i$) are computed over a selected frequency range ($F_{selected}$). The one or more processors are configured to output the LDF signal ($<v>$).

Computing the PSD $S_i(f)$ of the photodetector output signal for a series of time intervals ($t_i$) for example comprises computing a short time Fourier transform (STFT). In particular, computing the PSD may comprise computing the magnitude squared of the STFT.

The inventor found that, looking at the PSD of the photodetector signal, the frequency range in which the physiological information is found varies. Therefore, the inventor proposes to compute a measure of the amount of physiological information in the signal and then use said measure to select an adequate frequency range for further computations. For example, an optimum frequency range is selected.

In some embodiments, a first series of power spectral densities is used to determine the selected frequency range, which is then used for computing LDF signal(s) from a second, subsequent, series of power spectral densities. In other embodiments, a first series of power spectral densities is used to determine the selected frequency range, which is then used for computing LDF signal(s) from the same first series of power spectral densities.

The system may comprise multiple photodetectors. Thus, where the present application refers to "photodetector", alternatively multiple photodetectors are used according to the invention. In a first example, the output signals of the photodetectors are combined, e.g. by summing or averaging, and the power spectral density $S_i(f)$ is computed from the result. In a second example, each photodetector signal is processed independently of the other, and the resulting LDF signals $<v>$ are combined, e.g. by summing or averaging. In these example, the measure of the amount of physiological information can be computed from the combined signals, or the individual photodetector signals, or both.

The photodetector is for example a photodiode (generating a 1D signal). In another example, the photodetector is a photodiode array, a photodiode matrix or a camera (generating a 2D signal). For example, the camera may be a CCD camera. When a 2D photodetector is used, the 2D signal is preferably converted into one or more 1D photodetector output signals. For example, each pixel of a camera is processed as a separate photodetector output signal. In another example, an average of the pixel values of a group of pixels of the camera is computed and used as photodetector output signal. For example, an average over all pixels of the camera is computed to obtain a single photodetector output signal for use in subsequent computations. Instead of an average, a median, interquartile mean or other central tendency may be used.

According to a first aspect, the selected frequency range ($F_{selected}$) is determined based on a measure of amount of physiological information in LDF signals computed for a number of different frequency ranges.

In particular, according to the first aspect the one or more processors are configured to perform at least the following steps to determine the selected frequency range $F_{selected}$. A power spectral density ($S_i(f)$) is computed of the photodetector output signal for a series of time intervals ($t_i$), thereby obtaining a series of power spectral densities. For each respective frequency range $F_j$ out of P different frequency ranges ($F_{j=1\ to\ P}$), a measure of the amount of physiological information ($Q_j$) is computed for a LDF signal $<v_{Fj}>$ that is computed by computing moments ($M_i$) of the PSDs ($S_i(f)$) over the respective frequency range ($F_j$). The selected frequency range ($F_{selected}$) is then determined as the frequency range ($F_j$) for which the computed measure of amount of physiological information ($Q_j$) fulfills a predetermined criterion.

The one or more processors are further configured to output an LDF signal computed using the selected frequency range. For example, this includes an LDF signal that was computed during determination of the selected frequency, i.e. the LDF signal $<V_{Fj}>$ with $Fj=F_{selected}$. Alternatively or additionally, the selected frequency range is used to compute LDF signal(s) from subsequent photodetector output signals.

According to a second aspect, the selected frequency range ($F_{selected}$) is determined based on a measure of amount of physiological information in spectra of the photodetector output signal. In particular, determining the selected frequency range comprises computing a spectrum of the photodetector output signal for a series of time intervals ($t_i$), thereby obtaining a series of spectra. A measure of the amount of physiological information ($Q_f$) in said spectra is, for a number of different frequencies, is then computed. The selected frequency range ($F_{selected}$) is then determined as the range of frequencies (f) for which the computed measure of amount of physiological information ($Q_f$) fulfills a predetermined criterion. An LDF signal is computed using the selected frequency range, and the LDF signal is output.

Preferably, the spectra are PSDs of the photodetector output signal. Alternatively, the spectra are amplitude spectra of the photodetector output signal.

According to both the first aspect and the second aspect, a frequency range is selected based on a measure of amount of physiological information. The selected frequency range ranges from a lower frequency bound $f_{min}$ to an upper frequency bound $f_{max}$. Selecting the frequency range for example comprises selecting the upper frequency bound $f_{max}$, or selecting the lower frequency bound $f_{min}$, or selecting both the upper and lower frequency bound. In a current preferred embodiment, the lower frequency bound $f_{min}$ is predetermined (fixed) and selecting the frequency range comprises selecting the upper frequency bound $f_{max}$.

For example, the predetermined criterion comprises a threshold criterion. For example, if the measure $Q_i$ increases for increasing amount of physiological information (e.g. positive correlation), the threshold criterion comprises determining whether the measure exceeds a predetermined threshold. In another example, if the measure decreases for increasing amount of physiological information (e.g. negative correlation), the threshold criterion comprises determining whether the measure is below a predetermined threshold.

In another example, the predetermined criterion is indicative of a maximum amount of physiological information. For example, the frequency range corresponding to the maximum value of $Q_i$ is selected (in case $Q_i$ increases for increasing amount of physiological information) or the frequency corresponding to the minimum value of $Q_i$ is selected (in case $Q_i$ decreases for increasing amount of physiological information).

Optionally, the predetermined criterion additionally includes a predetermined lower limit for the measure $Q_i$. For example, if $Q_i$ is below the predetermined lower limit, the signal does not have sufficient quality to perform the LDF measurement. In that case, the method may fall back to the previously selected frequency range or to a predetermined default frequency range.

In some embodiments, the predetermined criterion comprises more than one criterion. For example, the method comprises a step of determining whether the bandwidth of the selected frequency range is below a minimum bandwidth, and, if it is determined that the bandwidth is below the minimum bandwidth, increasing the bandwidth to the minimum bandwidth, e.g. by increasing the upper frequency bound $f_{max}$ and/or lowering the lower frequency bound $f_{min}$. For example, the minimum bandwidth is 500 Hz.

Preferred embodiments are defined in the dependent claims and in the following paragraphs.

Embodiments of the First Aspect

In an embodiment of the first aspect, the measure of the amount of physiological information ($Q_i$) comprises a ratio between energy in a predetermined low frequency range of the respective LDF signal $<v_{F_j}>$ and energy in a predetermined high frequency range respective LDF signal $<v_{F_j}>$.

In an embodiment of the first aspect, the measure of the amount of physiological information ($Q_i$) comprises Shannon entropy of the respective LDF signal $<v_{F_j}>$.

In an embodiment of the first aspect, the measure of the amount of physiological information ($Q_i$) comprises a difference between the maximum and minimum points of the respective LDF signal $<v_{F_j}>$. In other words, the measure comprises a mean AC envelope.

In an embodiment of the first aspect, computing the measure of the amount of physiological information comprises determining a heart rate from the respective LDF signal $<v_{F_j}>$, and obtaining a reference heart rate, wherein the measure of the amount of physiological information ($Q_i$) comprises the difference between the heart rate determined from the respective LDF signal and the reference heart rate.

Preferably, the reference heart rate is obtained from a heart rate sensor. Alternatively, the heart rate is obtained from the output signal of the photodetector(s). For example, a heart rate is extracted from an LDF signal computed from the photodetector signal(s) without frequency optimization, e.g. an LDF signal computed over a broad frequency range (broader than all of the predetermined frequency ranges). This heart rate is then used as reference heart rate. In another example, the one or more processors maintain a running average of the heart rate of the LDF signals, e.g. over a period of 10-30 s, and the running average is used as a reference heart rate In this case, the measure $Q_i$ increases for decreasing physiological information: an increasing difference between the heart rate computed from the LDF signal and the heart rate obtained from the sensor is indicative of decreasing physiological information.

In an embodiment of the first aspect, computing the measure of the amount of physiological information in the respective LDF signal $<v_{F_j}>$ comprises: subdividing the LDF signal $<v_{F_j}>$ into individual LDF pulses.

In a further embodiment, computing the measure of the amount of physiological information comprises computing the number of individual LDF pulses within a predetermined time span.

For example, the number of individual LDF pulses is compared to an expected number of LDF pulses. The expected number of LDF pulses is computed as a function of heart rate, e.g. as obtained from a heart rate sensor. For example, the measure of amount of physiological information is greater when the computed number of pulses matches the expected number, and smaller when the computed number of pulses does not match the expected number pulses. For example, computing the measure of the amount of physiological information comprises computing a ratio between the measured number of LDF pulses and the expected number of LDF pulses.

For example, the one or more processors compute the minimum of $N_{measured}/N_{expected}$ and $N_{expected}/N_{measured}$, Wherein $N_{expected}$ is the expected number of pulses (e.g. based on heart rate obtained from a heart rate sensor) and $N_{measured}$ is the number of pulses measured in the LDF signal. In this example, a value of 1 represents an exact match between measured and expected number of pulses. The lower the calculated value is, the greater the mismatch between the measure and expected number.

In a further embodiment of the first aspect, a central tendency of the individual LDF pulses is determined to obtain an ensemble LDF pulse, and the measure of the amount of physiological information is computed from the ensemble LDF pulse. For example, the central tendency is an average, i.e. the ensemble LDF pulse is obtained by averaging the individual LDF pulses.

In a further embodiment, computing the measure further comprises determining the average amplitude of the first N harmonics of the individual LDF pulses, wherein N is an integer greater than 1. In a first example, the first N harmonics are calculated from the ensemble LDF pulse. In a second example, the average of the first N harmonics is calculated for each individual LDF pulse, and then the averages are averaged.

Preferably, obtaining the ensemble LDF pulse comprises time aligning the individual LDF pulses. The ensemble LDF pulse more accurately represents the central tendency (e.g. average) of the individual LDF pulses when the ensemble is computed on time aligned LDF pulses. For example, when computing the ensemble as an average of the individual pulses, an incorrect time-alignment will affect the shape of the ensemble such that it no longer represents a true average shape of the individual LDF pulses. Moreover, incorrect time alignment increases the amount of noise in the signal and therefore it is more difficult to detect features in the resulting LDF signal. Incorrect time alignment also increases the noise floor in the frequency domain and therefore fewer number of harmonics can be detected above the noise floor.

Time alignment may for example be achieved using an external trigger, e.g. a trigger obtained from an ECG sensor and/or a PPG sensor. In another example, a gradient of the individual LDF pulses is calculated, and the time point where the gradient has its maximum is identified as a time point for alignment. All LDF pulses are then time shifted such that said time points for alignment are aligned.

Embodiments of the Second Aspect

In an embodiment of the second aspect, determining the selected frequency range ($F_{selected}$) comprises obtaining one or more trigger signals indicative of a timing of individual LDF pulses. Using the one or more trigger signals, a spectrogram X(f,t) for each individual LDF pulse is determined from the spectra ($S_i(f)$).

In this embodiment, the step of computing the measure of the amount of physiological information ($Q_f$) comprises, computing the measure ($Q_f$) from the spectrograms.

The one or more trigger signals are indicative of a timing of LDF pulses. For example, the one or more triggers is/are indicative of an onset or rising edge of an LDF pulse or of a peak of the LDF pulse. The trigger signal is for example obtained from a sensor, such as an ECG (electrocardiography sensor) or PPG (photoplethysmography) sensor. As LDF, ECG and PPG signals follow the cadence of cardiac cycle, ECG and/or PPG signals can be used to obtain a trigger signal for identifying individual LDF pulses. This holds true even when some offset exists between the onset of an ECG or PPG signal and LDF pulses. In another example, the trigger signals are obtained from an analysis of the photodetector output signal itself. For example, an LDF signal is determined from the photodetector output signal (as described above), and pulse detection is performed on the LDF signal, e.g. by detecting a rising edge, a peak or a threshold crossing. The detection of the LDF pulse in the LDF signal is then used to generate the trigger signal.

In a further embodiment, an ensemble spectrogram ($X_E$(f,t)) is determined from the spectrograms of individual LDF pulses. The ensemble spectrogram comprises a central tendency of the spectrogram of the individual LDF pulses. In this embodiment, the step of computing the measure of the amount of physiological information ($Q_f$) comprises, computing the measure ($Q_f$) from the ensemble spectrogram. For example, the ensemble spectrogram $X_E$(f,t) comprises an average, median or interquartile mean of the spectrogram of the individual LDF pulses.

The ensemble spectrogram may be considered as a "template" for the spectrogram of the individual LDF pulses. By basing the measure of the amount of physiological information on the ensemble spectrogram rather than on individual spectrograms, the computation becomes less prone to outliers (e.g. distorted signals).

In an embodiment, the measure of the amount of physiological information comprises a dispersion d(f) of the spectra, as a function of frequency (f).

Preferably, the dispersion d(f) is normalized. For example, the dispersion d(f) comprises a standard deviation or variance. Preferably, the dispersion d(f) comprises a normalized standard deviation or normalized variance. For example, the standard deviation is normalized over the mean for the respective frequency.

Preferably, the predetermined criterion comprises a threshold criterion for the dispersion d(f). For example, the selected frequency range is determined as the frequency range over which the normalized standard deviation is above or below the threshold. The threshold is for example set as the median or mean of the dispersion d(f).

In a further embodiment, the measure of the amount of physiological information comprises a dispersion d(f) of the ensemble spectrogram $X_E$(f,t) as a function of frequency f. Alternatively, the measure of the amount of physiological information comprises a dispersion d(f) of the spectrogram X(f,t) of individual LDF pulses. In these two embodiments, the predetermined criterion preferably comprises a threshold criterion for the dispersion d(f).

Embodiments of the First or Second Aspect

In an embodiment of the first or second aspect, moments are computed as a weighted moment. For example, the moments are computed as a weighted first moment, a weighted second moment, or a combination thereof.

In an embodiment of the first or second aspect, a system comprises a wearable device comprising the light source and the photodetector.

In a first example, the wearable device further comprises the one or more processors for performing the computations. In a second example, the wearable device comprises a communication module for sending the photodetector output signal to the one or more processors, e.g. over a wireless connection.

In both the first and second aspect, the selected frequency range may be determined based on a first series of spectra (e.g. PSDs), after which the determined frequency range is used for computing the LDF signal from a second, subsequent, series of spectra (e.g. PSDs). Alternatively, the selected frequency range is determined based on a first series of spectra (e.g. PSDs), after which the determined frequency range is used for computing the LDF signal from the same first series of spectra (e.g. PSDs).

The invention further relates to a computer program. The computer program comprises instructions which, when executed by a computing device, execute the method according to any of the embodiments described herein. For example, the computer program is executable by a processor of a wearable device. The present disclosure further relates to a non-transitory computer-readable medium storing said computer program.

The same technical effects as described above in relation to the system apply to the method of the invention. Moreover, any features of the system described above can similarly be applied in the method. Preferably, the method is performed using the system of any of the embodiments of this disclosure.

BRIEF DESCRIPTION OF THE DRAWINGS

In the following, example embodiments will be described with reference to the drawings, wherein:

FIG. 1 shows a cross section of a wearable device or system for performing a LDF measurement of a blood perfused tissue;

FIG. 2 shows a schematic drawing of the system of FIG. 1;

FIG. 3 is a flow diagram of a general method for determining an LDF signal from a photodetector output, according to embodiments of the invention;

DETAILED DESCRIPTION OF THE DRAWINGS

Figures 4, 5:
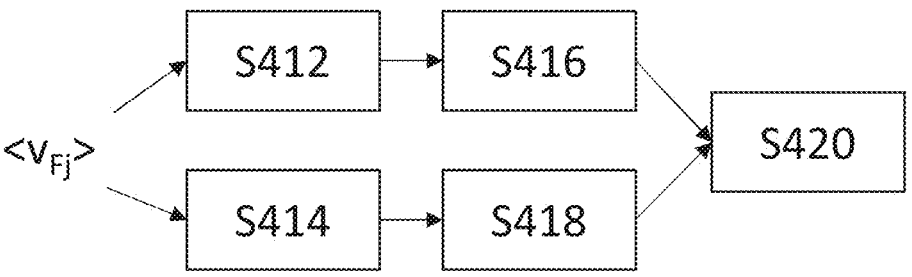
FIG. 4 is flow diagram of a method for selecting a frequency range for determining the LDF signal, according to an embodiment of the first aspect of the invention.
FIG. 5 is flow diagram of exemplary sub-steps for step S404 of FIG. 4.

A first embodiment of the invention is depicted in FIG. 1. The figure shows a cross section view of a body-worn device or system 10 and a cross-sectional view of a region of blood perfused tissue 30. The device 10 comprises a laser 12 (e.g. a laser diode such as a VCSEL). The coherent light 122 of the laser 12 exposes and penetrates the skin 300 and other parts of tissue 30 at exposed tissue region 32.

Discontinuities of optical properties in the tissue 30 can scatter the laser light in other directions than that of the incident direction, wherein moving discontinuities 34, e.g. blood cells, moving in blood vessels 301 can Doppler-shift the radiation. The Doppler shifting is related to a blood speed and can thus be used to derive a measure of blood speed (e.g. LDF).

The device 10 comprises a photodetector 16 arranged to receive scattered light from the tissue 30 and to generate a corresponding output signal 164. The drawing illustrates the photodetector 16 receiving scattered light 162 from the moving blood cells 34. Additionally, the photodetector 16 receives scattered light from stationary discontinuities (not illustrated). The light from moving discontinuities 34 and stationary discontinuities interferes, resulting in a measurable Doppler shift.

The device 10 further comprises a processor 18 for generating an LDF signal based on the photodetector output 164. The processor 18 is not shown in the cross section of FIG. 1. Reference is made to FIG. 2, that shows a schematic drawing of the laser 12, photodetector 16 and processor 18. The lines in FIG. 2 indicate the functional connection between the processor 18 and the laser 12, and between the processor 18 and the photodetector 16. The processor 18 is configured to control the laser 12 to emit laser light 122 onto the skin 300. The processor 18 is further configured to process the output 164 of the photodetector 16.

In the illustrated examples, the processor 18 is a digital processor and the photodetector output 164 is a digital signal. The device 10 may include an ADC to convert analogue output of the photodetector 16 into the digitized photodetector output 164. Alternatively, processor 18 may comprise an analogue processing circuit for operating on an analogue photodetector signal.

The processing of the photodetector output 164 to produce an LDF signal is illustrated in the flow diagrams of FIGS. 3-6. FIG. 3 describes the general method for producing an LDF signal from photodetector output 164, whereas FIGS. 4-6 describes determining a suitable frequency range for performing the method of FIG. 3.

In step S400 (FIG. 3), a power spectral density $S_i(f)$ is computed for consecutive time intervals ($t_i$, with i=1, 2, . . . , $\psi$) of the photodetector output 164 to obtain a series of power spectral densities. This is done by computing a short-time Fourier transform (STFT), $\Omega(t_i, f)$, of the photodetector signal 164 and computing the power spectral densities $S_i(f)$ as the square of the magnitude of the STFT: $S_i(f) |\Omega(t_i,f)|^2$.

The time interval is predetermined and preferably smaller than a typical duration of an LDF pulse. In the present examples, the time intervals $T_i$ do not overlap. Alternatively, the time intervals $T_i$ may overlap. The time interval determines the sampling rate (or vice versa). The sampling rate is set to at least 100 Hz. With a sampling rate of 100 Hz, a frequency response up to 50 Hz is obtained (according to the Nyquist criterion). With a heart rate of 180 bpm, up to 17 harmonics can be detected using this sampling rate. This is considered sufficient. A sampling rate of at least 100 Hz corresponds to a time interval of 10 ms or shorter. For example, the predetermined time interval is 1 ms-10 ms. In some embodiments, higher sampling rates are used, e.g. 200 Hz, 400 Hz or even higher, corresponding to predetermined time intervals of 5 ms, 2.5 ms or even shorter.

Step S402 then computes a moment M(i) of each of the power spectral densities $S_i(f)$ computed in step S400. The $N^{th}$ moment $M_N(i)$ of power spectral density $S_i(f)$ is computed as:

$$M_N(i) = \sum_{f_{min}}^{f_{max}} f^N \cdot S_i(f)$$

(equation 1)

where:

$M_N(t)$ is the $N_{th}$ moment of the spectral density $S_i(f)$ at time $t_i$, $f_{min}$ and $f_{max}$ are the lower and upper bounds of the frequency range over which the moment is to be calculated, and $S_i(f)$ is the power spectral density at time $t_i$.

The magnitude of the first moment $M_1(i)$ is proportional to the average Doppler shift of the light received by the photodetector 16 and proportional to the intensity of the light. The first moment may be normalized in order to remove or reduce the dependency of the intensity by dividing it by the average determined over the same frequency band.

$$v(i) = \frac{M_1(i)}{M_0(i)} \qquad \text{(equation 2)}$$

wherein:

$v(i)$ is the average Doppler shift at time $t_i$, $M_0(i)$ is the average spectral density at time $t_i$.

Optionally, a weighted $N^{th}$ moment is computed, wherein the summation includes a frequency-dependent weighting factor $w(f)$:

$$M_N(i) = \sum_{f_{min}}^{f_{max}} w(f) \cdot f^N \cdot S_i(f) \qquad \text{(equation 3)}$$

The weighting factors $w(f)$ may for example be chosen to provide less weight to the frequencies near $f_{min}$ and near $f_{max}$ than to more central frequencies. For example, the weighting factor is based on a triweight function or a Gaussian function.

Optionally, the weighting factor $w(f)$ is set to zero for a small subset of frequencies within the frequency range ($f_{min}$, $f_{max}$). This effectively excludes these frequencies from the computation. The number of frequencies excluded is small, e.g. less than 20% of the frequency range. In other words, most of the weighting factors are set to non-zero values, preferably at least 80% of the weighting factors.

When computing a weighted moment, preferably a predetermined set of weighting factors $w_j(f)$ (j=1 to P) is used for each of the predetermined frequency ranges $F_j$ (j=1 to P).

Likewise, a weighted and normalized $N^{th}$ moment can be computed. Preferably, a weighted and normalized $1^{st}$ moment is calculated as above, wherein both $M_1(i)$ and $M_0(i)$ are computed using a weighting factor $w(f)$ or $w_j(f)$. Optionally, more than one moment is computed, e.g. a first moment (optionally normalized and/or weighted) and a second moment (optionally normalized and/or weighted).

As illustrated in FIG. 3, step S402 receives the selected frequency range $F_{selected}$ as input. In this example, $F_{selected}$ includes the variable $f_{max}$, while $f_{min}$ is fixed to 500 Hz. The inventor found that the quality of the LDF signal is highly dependent on the selected frequency range. Selecting a frequency range that results in a good quality LDF signal is an object of the present invention. Different methods for determining the frequency range $F_{selected}$ will be described below with reference to FIG. 4 and further.

The end result of step S402 is a series of average Doppler shifts $\langle v_i \rangle = M_1(i)/M_0(i)$ for times $t_i$ ($t_1$ to $t_\psi$). The series is denoted in FIG. 3 as the vector $\langle v \rangle$ ($\langle v \rangle = \langle v_1 \rangle, \langle v_2 \rangle, \ldots \langle v_\psi \rangle$), and represents the LDF signal.

FIG. 4 shows a first embodiment of a method for performing a LDF measurement that includes steps for selecting a frequency range $F_{selected}$. Step 400 is the same as in FIG. 3 and computes, from the photodetector output 164, power spectral densities $S_i(f)$ for consecutive time intervals ($t_i$, with i=1, 2, . . . , $\psi$). Step S401 initializes a frequency range variable $F_j$ for a loop L1. Loop L1 loops through a predefines set of P frequency ranges (i.e. $F_j$ with j=1 to P). For example, the frequency ranges $F_j$ comprise P predefined frequency ranges that span 500 Hz each. In other examples, the frequency ranges $F_j$ comprise P predefined frequency ranges with different bandwidths, e.g. frequency ranges with the same minimum frequency $f_{min}$ but different maximum frequency $f_{max}$. In step S401, j is set to 1 and then the method continues to loop L1.

Within loop L1, step S402 is executed in the same manner as described with reference to FIG. 3. In this example, step S402 computes a normalized first moment of each of the spectral densities $S_i(f)$ computed in step S400. The moments computation is executed for the current frequency range $F_j$. The result of S402 is a series of average Doppler shifts $\langle v_{Fj,i} \rangle = M_1(i)/M_0(i)$ for times $t_i$ ($t_i$ to $t_\psi$) for the frequency range $F_j$. The series is denoted in FIG. 4 as the vector $\langle v_{Fj} \rangle$ ($\langle v_{Fj} \rangle = \langle v_{Fj,1} \rangle, \langle v_{Fj,2} \rangle, \ldots \langle v_{Fj,\psi} \rangle$), and represents an LDF signal.

In step S404, a measure of the amount of physiological information is computed for the specific frequency range $F_j$. This measure is denoted as $Q_j$ and may also be referred to as "figure of merit" or "FOM". More details of the computation of $Q_j$ will be described below. Preferably, $Q_j$ is a scalar or a vector with a predetermined number of vector elements, to allow comparison between different measures $Q_j$ computed for different $F_j$.

Step S406 checks whether the loop L1 has been performed for all frequency ranges $F_j$. Particularly, step S406 checks whether the condition j=P is true. If the condition is false, the method increments j by 1 in step S408, and returns to step S402. If the condition is true, all frequency ranges $F_j$ have been processed, and the method moves to step S410.

When arriving at step S410, the method has computed—and stored—the measure $Q_j$ for all P frequency ranges $F_j$. Step S410 then selects one of the frequency ranges $F_j$ based on the computed measures $Q_j$. In particular, steps S410 determines whether $Q_j$ fulfils a predetermined criterion. For example, step S410 determines the maximum or minimum of the computed $Q_j$ values. The selected frequency is denoted as $F_{selected}$. Optionally, $F_{selected}$ is output.

Step S410 then outputs the LDF signal $\langle v_{Fselected} \rangle$ that corresponds to the selected frequency $F_{selected}$. Preferably, in the loop L1, the vectors $\langle v_{Fj} \rangle$ are stored, such that in step S410, the output $\langle v_{Fselected} \rangle$ does not have to be recalculated.

Alternatively or additionally, the selected frequency $F_{selected}$ thus is used for computing an LDF signal from a subsequent series of PSDs. For example, $F_{selected}$ is used in the LDF computation for consecutive time intervals ($t_1$, with i=$\psi$+1, $\psi$+2, . . . ).

In the following, different options for the computation of the measure of the amount of physiological information $Q_j$ are described. $Q_j$ may be based on a single metric of the amount of physiological information, but preferably $Q_j$ is based on a combination of different metrics for the amount of physiological information. For example, a number of different metrics is combined in a vector $Q_j$, or a weighted average of the different metrics is computed to arrive at a single scalar $Q_j$.

A first example of computing a metric for $Q_j$ is illustrated in FIG. 5. In this example, the metric comprises a ratio between low frequency energy and high frequency energy of the LDF signal $\langle v_{Fj} \rangle$ for frequency range $F_j$. The ratio is calculated (i.e. in step S404 of FIG. 4), by inputting $\langle v_{Fj} \rangle$ into processing steps S412 and S414. Step S412 applies a low pass (LP) filter to $\langle v_{Fj} \rangle$ and step S414 applies a high pass (HP) filter to $\langle v_{Fj} \rangle$. The cutoff frequencies of the filters are preferably chosen to be the same. Cutoff frequencies can be typically above 5 Hz (such that, for a heart rate of 60 bpm, the first five harmonics of the signal are included). Optionally, the LDF signal $<v_{Fj}>$ is pre-processed by applying a further high pass filter with a cut-off frequency around 0.5 Hz, to suppress low frequency movement artefacts. In steps S416 and S418, the energy of the low and high pass filtered signal is computed. The energy of a signal is defined as the integral of the squared magnitude of the signal. For a discrete signal this boils down to the summation of the squared magnitudes of the signal values.

Step 420 computes a ratio $R_{Fj}$ between the two energies. The ratio gets higher for the signal with more physiological content, since the physiological information typically resides in a lower part of the frequency spectrum.

In a second example of a metric for $Q_j$, the spectral entropy $E_{Fj}$ of the signal $<v_{Fj}>$ is computed. The spectral entropy is a measure of the signal's spectral power distribution. The spectral entropy treats the signal's normalized power distribution in the frequency domain as a probability distribution and calculates the Shannon entropy of the distribution. The higher the spectral entropy, the more random the signal is. Therefore, this metric gets lower for signals having a larger amount of physiological information.

In a third example of a metric for $Q_j$, a difference $AC_{Fj}$ between maximum and minimum points of the LDF signal $<v_{Fj}>$ is computed. This is also referred to as "mean AC envelope". This metric gets higher when more physiological content is present in the signal. For example, $AC_{Fj}$ is computed as $AC_{Fj}=\max(<v_{Fj}>)-\min(<v_{Fj}>)$.

In a fourth example of computing a metric for $Q_j$, a heart rate is estimated from the respective LDF signal $<v_{Fj}>$. For example, the estimation computes the number of peaks in the LDF signal per unit time. In addition, a heart rate is obtained from a heart rate sensor. Then, a difference or ratio between the estimated heart rate $HR_{estimated}$ (determined from $<v_{Fj}>$) and the heart rate $HR_{measured}$ obtained from the heart rate sensor. This results in a metric $\Delta_{Fj}$. For example $\Delta_{Fj}=HR_{estimated}-HR_{measured}$ or $\Delta_{Fj}=HR_{estimated}/HR_{measured}$ Preferably, $Q_j$ is computed by combining several of the metrics described above, e.g. by computing a weighted combination. For example, to compute a measure $Q_j$ that increases for an increasing amount of physiological information, the metrics described above may be combined according to:

$$Q_j = w_1 R_{Fj} + w_2/E_{Fj} + w_3 AC_{Fj} + w_4 \Delta_{Fj},$$

wherein $w_i$ are predetermined weight factors. In this computation, the inverse of $E_{Fj}$ is used, as this metric decreases for increasing amount of physiological information, whereas the other metrics are multiplied by the weighting factor as they increase for increasing physiological content.

Figure 6:
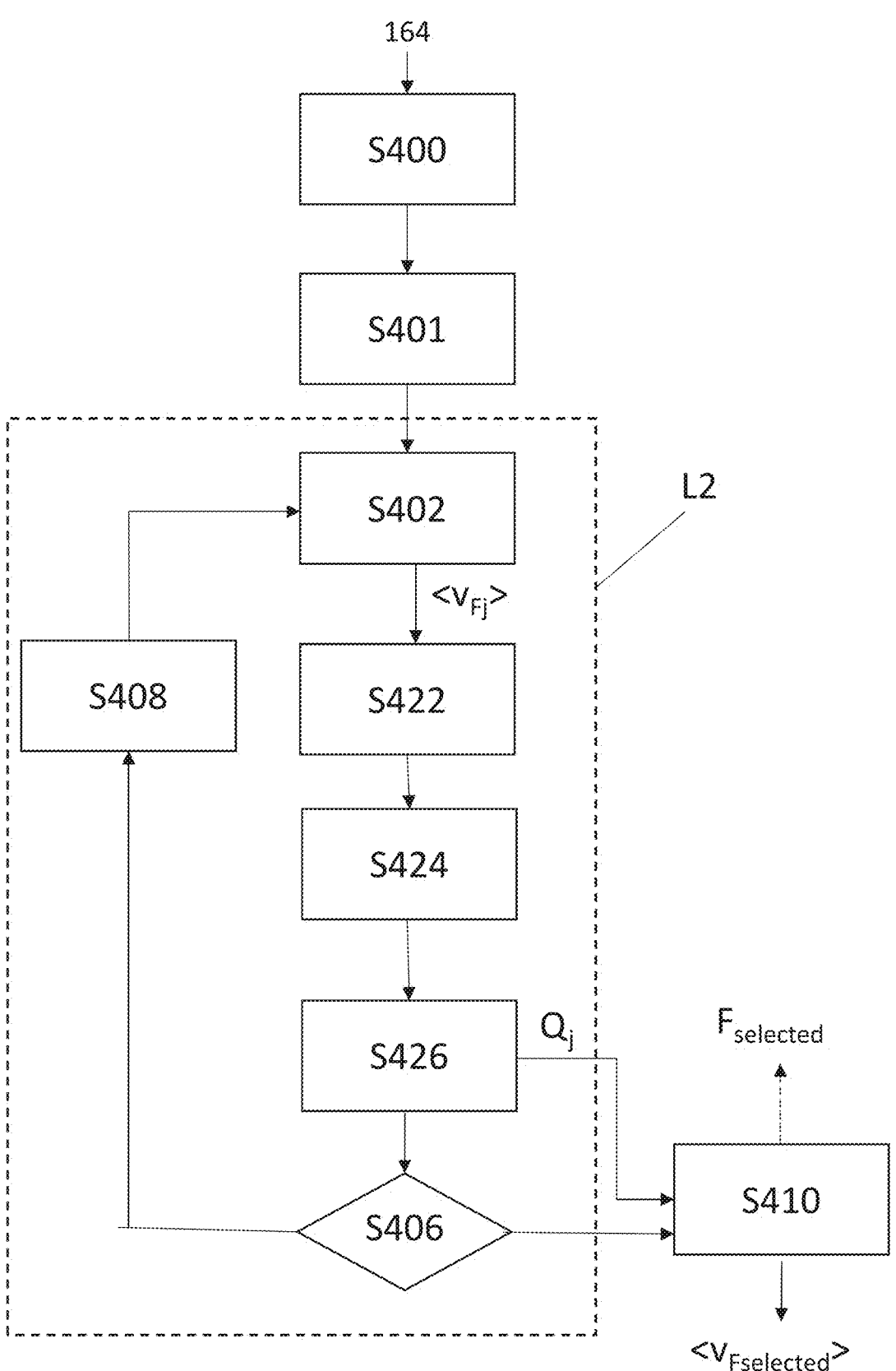
FIG. 6 is flow diagram of a method for selecting a frequency range for determining the LDF signal, according to another embodiment of the first aspect of the invention.

FIG. 6 illustrates computing $Q_j$ based on an ensemble LDF pulse. The ensemble LDF pulse is computed based on a central tendency of individual LDF pulses, e.g. as an average pulse. Steps S400, S401, S402 are identical to those described in relation to FIG. 4. In step S422, the LDF signal $<v_{Fj}>$ for the current frequency range $F_j$ is split into individual LDF pulses. Step S424 computes an average pulse based on the individual pulses computed in step S422. Step S426 determines the measure $Q_j$ based on the ensemble LDF pulse.

As in FIG. 4, step S406 check whether the loop L2 has been performed for all frequency ranges Fj. Particularly, step S406 checks whether the condition j=P is true. If the condition is false, the method increments j by 1 in step S408, and returns to step S402. If the condition is true, all frequency ranges $F_j$ have been processed, and the method moves to step S410. As previously described in relation to FIG. 4, step S410 selects a frequency range based on the computed measures $Q_j$, and the LDF signal $<v_{Fselected}>$ corresponding to the selected frequency range is output. Optionally, also $F_{selected}$ is output.

For example, the computation of $Q_j$ includes computing the metrics described above (energy ratio $R_{Fj}$, entropy $E_{Fj}$, AC envelope $AC_{Fj}$, heart rate difference $\Delta_{Fj}$) for the ensemble average computed in steps S424. Another example of a metric is the average amplitude of the first N harmonics of the ensemble LDF pulse, wherein N is an integer greater than 1. Preferably the first three harmonics are used for the computation.

In a further example, computation of $Q_j$ comprises computing an average of the first N harmonics divided by an estimate noise floor. The noise floor is estimated by computing a median of the part of the spectrum in between the detected harmonics.

Note that the metrics computed in FIGS. 4 and 6 may be combined. Particularly, the measure $Q_j$ may combine metrics computed from the signals $<v_{Fj}>$ and metrics computed from the ensemble average derived from the signals $<v_{Fj}>$.

Figure 7:
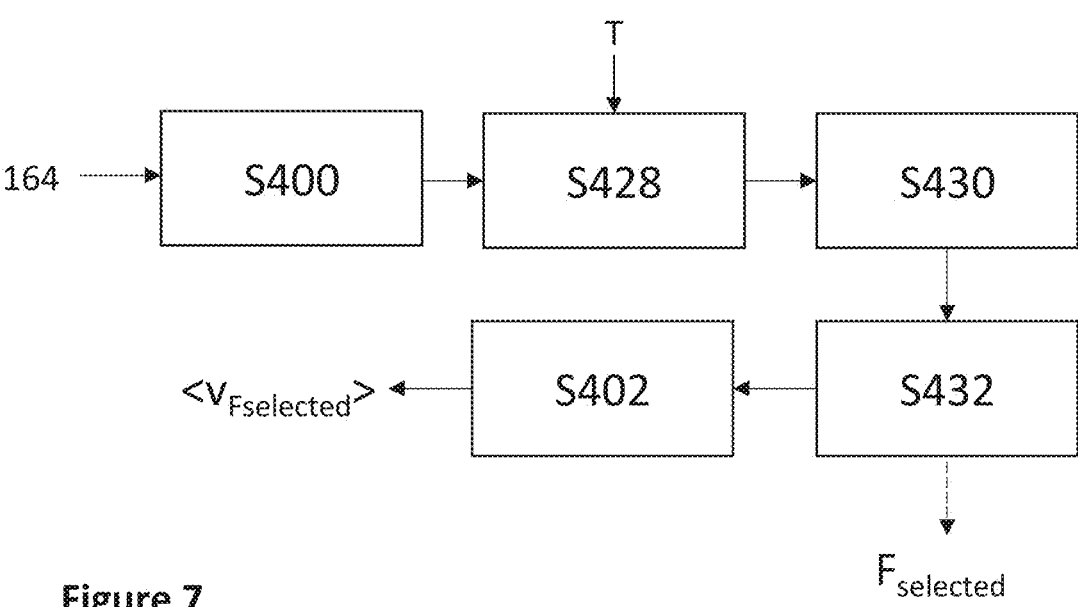
FIG. 7 is flow diagram of a method for selecting a frequency range for determining the LDF signal, according to an embodiment of the second aspect of the invention.

FIG. 7 illustrates an embodiment of a method for selecting the frequency $F_{selected}$, directly from the power spectral densities $S_i(f)$. Notably, the method of FIG. 7 does not require a loop for calculating moments for a number of different frequency ranges.

Figure 8:
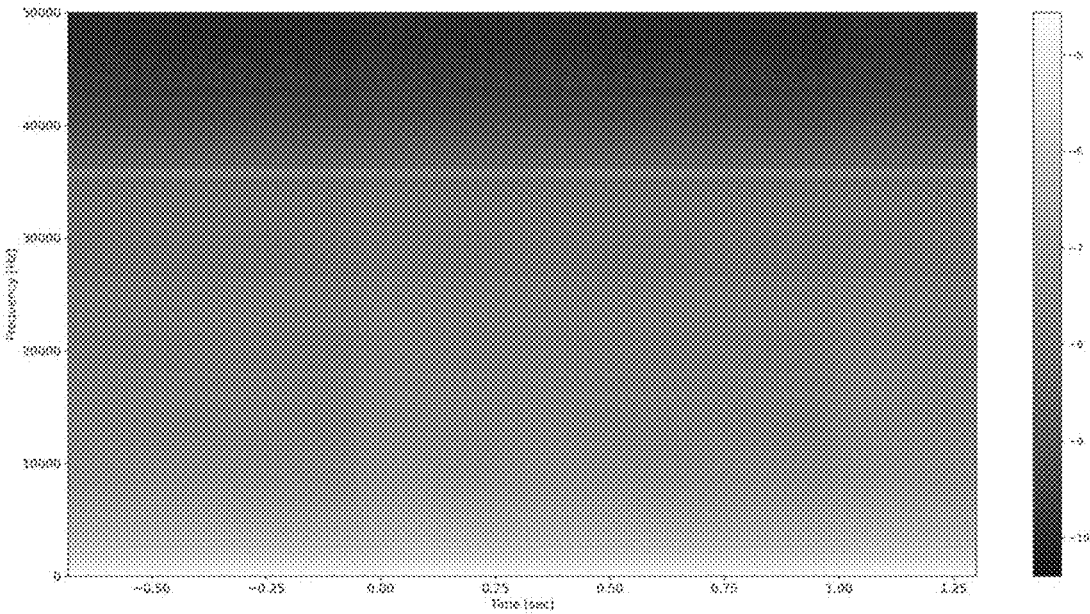
FIG. 8 shows an example of an ensemble average spectrogram of LDF pulses.

Step S400 is identical to step S400 of FIGS. 4 and 6: power spectral densities $S_i(f)$ are computed from the photodetector signal 164, for different discrete time point $t_i$. In step S428 the consecutive PSDs $S_i(f)$ are processed to generate an ensemble average spectrogram, i.e. a spectrogram representative of an average LDF pulse. Step S428 uses a trigger signal T to generate the ensemble average spectrogram. The trigger signals are indicative of timing of the LDF pulses. In this example, the trigger signal is obtained from an ECG sensor and indicates the start time of an ECG pulse. As ECG and LDF pulses both follow the cardiac cycle, the start time of an ECG pulse is indicative of the start time of an LDF pulse. In a first sub-step of S428, the PSDs $S_i(f)$ (i=1 to $\psi$) are subdivided into Z pulses, based on the timing information from the trigger signal T. The number of pulses Z is at least an order of magnitude smaller than $\psi$. For example, 1000 PSDs $S_i(f)$ are subdivided into 5 pulses comprising 200 PSDs $S_i(f)$ each. Each pulse thus corresponds to a different subset of the PSDs $S_i(f)$. The subset of PSDs $S_i(f)$ of a single LDF pulse describes a spectrogram X(f, t). In this notation, t is renumbered with respect to i, such that the spectrograms of the pulses span the same time window. In a second sub-step of S428, the spectrograms X(f, t) of the individual LDF pulse are averaged, to obtain an ensemble average spectrogram $X_E(f,t)$. An example of such an ensemble average spectrogram is illustrated in FIG. 8. In this figure, the horizontal axis represents t (time), and the vertical axis represents frequency (f). The colors indicate the magnitude of $X_E(f,t)$, on a logarithmic scale.

Figure 9:
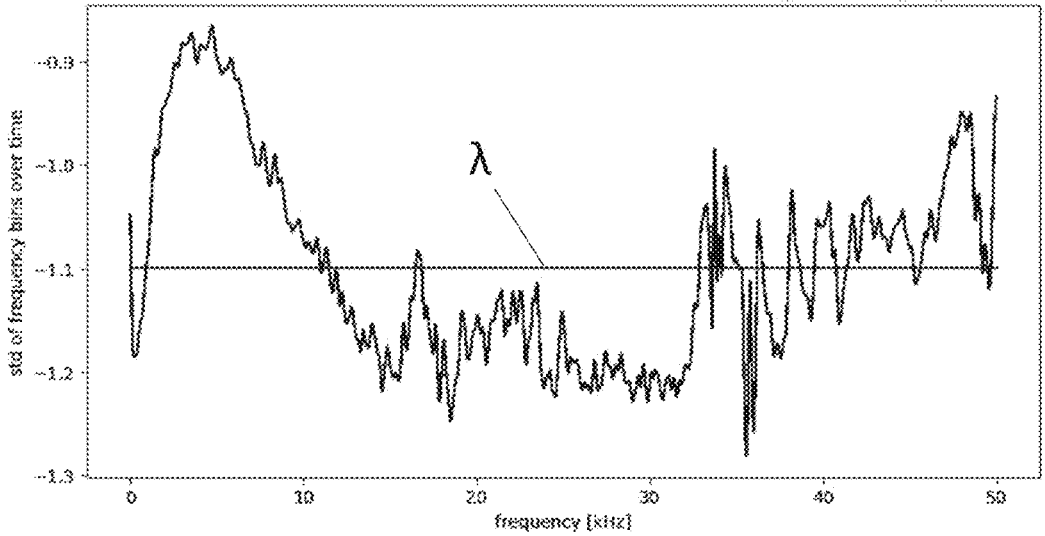
FIG. 9 shows a normalized standard deviation of the spectrogram of FIG. 8 (plot on a logarithmic scale)

In step S430, a dispersion d(f) is computed from the ensemble average spectrogram $X_E(f,t)$. In other words, for each frequency f of the spectrogram $X_E(f,t)$, the dispersion along the time axis is computed. In this example, the dispersion d(f) comprises the normalized standard deviation $\sigma(f)$. Specifically, the standard deviation is normalized by the mean. FIG. 9 shows a plot of the normalized standard 13
14 deviation $\sigma(f)$ computed from the spectrogram of FIG. 8, on a logarithmic scale. The horizontal axis represents frequency. The vertical axis represents the logarithm of the normalized standard deviation.

In step S432, the normalized standard deviation $\sigma(f)$ is compared to a threshold $\lambda$. The frequency where the threshold $\lambda$ is crossed for the first time while $\sigma(f)$ has a positive slope is determined as the minimum frequency, $f_{min}$, and the frequency where the threshold $\lambda$ is crossed for the first time while $\sigma(f)$ has a negative slope is determined as the maximum frequency, $f_{max}$. The result is a selected frequency range of $F_{selected}=(f_{min}, f_{max})$.

The threshold $\lambda$ may be a fixed value. Preferably however, the threshold $\lambda$ is determined as a central tendency of the normalized standard deviation $\sigma(f)$, e.g. the threshold $\lambda$ is selected as the mean or median of the normalized standard deviation $\sigma(f)$.

The result of step S432 is a selected frequency range $F_{selected}$. Referring back to FIG. 7, $F_{selected}$ may optionally be output by step S432. The next step in the process is step S402 that, as before, computes the LDF signal by calculating moments of the power spectral densities $S_i(f)$ over the selected frequency $F_{selected}$. The end result of the method is the LDF signal $<v_{FSelected}>$.

In the example of FIG. 7, the selected frequency range $F_{selected}$ is computed from a series of PSDs $S_i(f)$. Step S402 is then applied to the same series of PSDs to determine an LDF signal. Alternatively or additionally, step S402 is applied to a subsequent series of PSDs.

In the example of FIG. 7, steps S400 computes PSDs. Alternatively, step S400 of FIG. 7 computes an amplitude spectrum, e.g. as a magnitude of the STFT: $A_i(f)=|\Omega(t_i,f)|$.

The examples above describe the use of an output signal 164 of a single photodetector. Alternatively, the system comprises multiple photodetectors, and the processing by the one or more processors is based on the photodetector signals output by the photodetectors. In a first example, the photodetector signals are summed prior to step S400, such that the LDF signal can be computed from a single, combined photodetector signal. In a second example, each photodetector signal is processed independently of the other, and the resulting LDF signals are combined.

The examples above describe computing a "raw" moment (equation 1), a normalized "raw" moment (equation 2) or a weighted moment (equation 3). Alternatively, a central moment is computed, e.g. by replacing the term $f^N$ in equations 1-3 by $(f-f_c)^N$, wherein $f_c$ is a central frequency. The central frequency fc is for example computed as the normalized first raw moment (equation 2).

Figure 10:
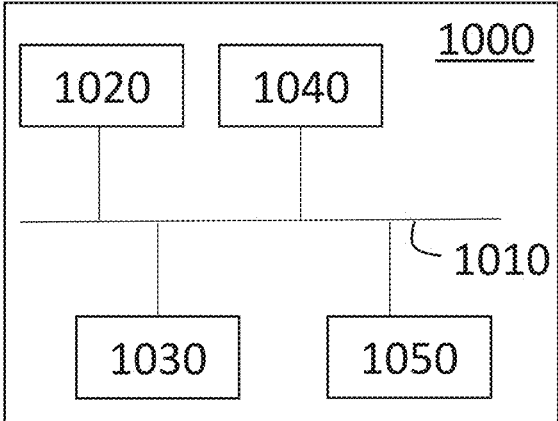
FIG. 10 schematically illustrates an exemplary computing device for implementing any of the method of the present disclosure.

FIG. 10 is a schematic view of an exemplary computing device 1000 for implementing the computer-implemented method of any embodiment of the present disclosure. The computing device 1000 includes some or all of: a processor 1020 (e.g., a CPU), a memory 1030 (e.g., a solid state drive, or SSD), a communication interface 1040 (e.g., a wireless network communication interface and/or input/output interface e.g. for receiving a signal of a photodetector), and a power supply 1050 that are communicatively coupled together via a bus connection 1010. It will be understood that any type of non-transitory computer readable storage device may be used as the memory 1030 in addition or alternative to an SSD. The communication interface 1040 or the bus connection 1010

For example, computing device 1000 may be implemented by one or more instances (e.g., articles, pieces, units, etc.) of processing circuitry such as hardware including logic circuits; a hardware/software combination such as a processor executing software; or a combination thereof. For example, the processing circuitry more specifically may include, but is not limited to, a central processing unit (CPU), an arithmetic logic unit (ALU), a digital signal processor, a microcomputer, a field programmable gate array (FPGA), a System-on-Chip (SoC), a programmable logic unit, a microprocessor, application-specific integrated circuit (ASIC), or any other device or devices capable of responding to and executing instructions in a defined manner. In some example embodiments, the processing circuitry may include a non-transitory computer readable storage device, or memory (e.g., memory 1030), for example a solid state drive (SSD), storing a program of instructions, and a processor (e.g., processor 1020) that is communicatively coupled to the non-transitory computer readable storage device (e.g., via a bus connection 1010) and configured to execute the program of instructions to implement the functionality of some or all of any of the devices and/or mechanisms of any of the example embodiments and/or to implement some or all of any of the methods of any of the example embodiments.

The invention claimed is:

1. A system for performing a laser Doppler flowmetry measurement of a blood perfused tissue, the system comprising:

a light source configured to emit coherent light to the blood perfused tissue;

a photodetector configured to receive a portion of the coherent light scattered by the blood perfused tissue and generate a photodetector output signal in response to receiving said portion; and one or more processors configured to determine a selected frequency range ($F_{selected}$) for computing a laser Doppler flowmetry signal (LDF signal), wherein the determining the selected frequency range ($F_{selected}$) includes computing a spectrum ($S_i(f)$) of the photodetector output signal for a series of time intervals ($t_i$), thereby obtaining a series of spectra, computing, for a number of different frequencies (f), a measure of an amount of physiological information ($Q_f$) in the spectra ($S_i(f)$), and determining the selected frequency range ($F_{selected}$) as a range of frequencies (f) for which the measure of the amount of physiological information ($Q_f$) fulfills a predetermined criterion, wherein the one or more processors are further configured to compute the LDF signal using the selected frequency range, and to output the LDF signal, wherein the measure of the amount of physiological information ($Q_f$) comprises a dispersion d(f) of the spectra, as a function of frequency (f), and wherein the predetermined criterion includes a threshold criterion for the dispersion d(f), and the determining the selected frequency range ($F_{selected}$) includes comparing the dispersion d(f) to a threshold $\lambda$, determining a minimum frequency ($f_{min}$) of the selected frequency range ($F_{selected}$) as a first frequency where the threshold $\lambda$ is crossed for a first time while the dispersion d(f) has a positive slope, such that the dispersion d(f) has a value that increases with increasing frequency across the first frequency while maintaining the positive slope across the first frequency, and determining a maximum frequency ($f_{max}$) of the selected frequency range ($F_{selected}$) as a second frequency where the threshold $\lambda$ is crossed for a first time while the dispersion d(f) has a negative slope, such that the dispersion d(f) has a value that decreases with increasing frequency across the second frequency while maintaining the negative slope across the second frequency.

2. The system of claim 1, wherein the determining the selected frequency range ($F_{selected}$) comprises:

obtaining a plurality of trigger signals, each trigger signal of the plurality of trigger signals indicative of a timing of a separate individual LDF pulse of individual LDF pulses of the LDF signal, the individual LDF pulses following a cadence of a cardiac cycle;

using the plurality of trigger signals, determining, from the spectra ($S_i(f)$), a separate spectrogram for each separate individual LDF pulse of the individual LDF pulses to determine spectrograms of the individual LDF pulses; and determining, from the spectrograms of the individual LDF pulses, an ensemble spectrogram ($X_E(f,t)$), comprising a central tendency of the spectrograms of the individual LDF pulses, wherein the dispersion d(f) is computed from the ensemble spectrogram ($X_E(f,t)$).

3. The system of claim 2, wherein the plurality of trigger signals are obtained from at least one of:

an ECG sensor (electrocardiography sensor) generating ECG signals that follow the cadence of the cardiac cycle, such that the plurality of trigger signals are obtained based on the ECG signals, or a PPG sensor (photoplethysmography sensor) generating PPG signals that follow the cadence of the cardiac cycle, such that the plurality of trigger signals are obtained based on the PPG signals.

4. The system of claim 1, comprising a wearable device comprising the light source and the photodetector.

5. A computer-implemented method for computing a laser Doppler flowmetry signal (LDF signal), the computer-implemented method comprising:

receiving a photodetector output signal from an LDF system; and determining a selected frequency range ($F_{selected}$) for computing the LDF signal, wherein the determining the selected frequency range ($F_{selected}$) includes computing a spectrum ($S_i(f)$) of the photodetector output signal for a series of time intervals ($t_i$), thereby obtaining a series of spectra, computing, for a number of different frequencies (f), a measure of an amount of physiological information ($Q_f$) in the spectra ($S_i(f)$), and determining the selected frequency range ($F_{selected}$) as a range of frequencies (f) for which the measure of the amount of physiological information ($Q_f$) fulfills a predetermined criterion, wherein the computer-implemented method further includes computing the LDF signal using the selected frequency range, and outputting the LDF signal, wherein the measure of the amount of physiological information comprises a dispersion d(f) of the spectra, as a function of frequency (f), and wherein the predetermined criterion includes a threshold criterion for the dispersion d(f), and the determining the selected frequency range ($F_{selected}$) includes comparing the dispersion d(f) to a threshold $\lambda$, determining a minimum frequency ($f_{min}$) of the selected frequency range ($F_{selected}$) as a first frequency where the threshold $\lambda$ is crossed for a first time while the dispersion d(f) has a positive slope, such that the dispersion d(f) has a value that increases with increasing frequency across the first frequency while maintaining the positive slope across the first frequency, and determining a maximum frequency ($f_{max}$) of the selected frequency range ($F_{selected}$) as a second frequency where the threshold $\lambda$ is crossed for a first time while the dispersion d(f) has a negative slope, such that the dispersion d(f) has a value that decreases with increasing frequency across the second frequency while maintaining the negative slope across the second frequency.

6. The computer-implemented method of claim 5, wherein the determining the selected frequency range ($F_{selected}$) comprises:

obtaining a plurality of trigger signals, each trigger signal of the plurality of trigger signals indicative of a timing of a separate individual LDF pulse of individual LDF pulses of the LDF signal, the individual LDF pulses following a cadence of a cardiac cycle;

using the plurality of trigger signals, determining, from the spectra ($S_i(f)$), a separate spectrogram for each separate individual LDF pulse of the individual LDF pulses to determine spectrograms of the individual LDF pulses; and determining, from the spectrograms of the individual LDF pulses, an ensemble spectrogram ($X_E(f,t)$), comprising a central tendency of the spectrograms of the individual LDF pulses, wherein the dispersion d(f) is computed from the ensemble spectrogram ($X_E(f,t)$).

7. The computer-implemented method of claim 6, wherein the plurality of trigger signals are obtained from at least one of:

an ECG sensor (electrocardiography sensor) generating ECG signals that follow the cadence of the cardiac cycle, such that the plurality of trigger signals are obtained based on the ECG signals, or a PPG sensor (photoplethysmography sensor) generating PPG signals that follow the cadence of the cardiac cycle, such that the plurality of trigger signals are obtained based on the PPG signals.

8. A non-transitory computer-readable medium storing a computer program, the computer program comprising instructions that, when executed by one or more processors, cause the one or more processors to execute the computer-implemented method according to claim 5.

\* \* \* \* \*